United States Patent [19]

Pesavento et al.

[11] Patent Number: 4,851,665
[45] Date of Patent: Jul. 25, 1989

[54] SYSTEM FOR SENSING IONS IN AQUEOUS SOLUTION

[75] Inventors: Philip V. Pesavento, Manhatten Beach; Joy W. Strawbridge, Camarillo, both of Calif.

[73] Assignee: Hughes Aircraft Company, Los Angeles, Calif.

[21] Appl. No.: 195,406

[22] Filed: May 16, 1988

Related U.S. Application Data

[63] Continuation of Ser. No. 907,269, Sep. 15, 1986.

[51] Int. Cl.$^4$ ............................................. H01J 5/16
[52] U.S. Cl. .................................. 250/227; 356/436
[58] Field of Search .................... 250/227, 231 R, 573, 250/577, 551; 356/434–436, 442, 420, 409

[56] References Cited

U.S. PATENT DOCUMENTS

| | | | |
|---|---|---|---|
| 2,324,304 | 7/1943 | Katzman | 356/442 |
| 2,580,500 | 1/1952 | Albert | 356/442 |
| 3,263,553 | 8/1966 | Baruch | 250/573 |
| 3,819,278 | 6/1974 | Muller | 356/442 |
| 3,994,590 | 11/1976 | Di Martini et al. | 356/409 |
| 4,134,022 | 1/1979 | Jacobsen | 250/577 |
| 4,241,738 | 12/1980 | Lubbers et al. | |
| 4,521,684 | 6/1985 | Gilby et al. | 250/231 R |
| 4,534,651 | 8/1985 | Minikane | 250/227 |
| 4,607,160 | 8/1986 | Sakakino | 250/227 |
| 4,644,154 | 2/1987 | Brogardh et al. | 250/227 T |

FOREIGN PATENT DOCUMENTS

0047094 3/1982 European Pat. Off. .

OTHER PUBLICATIONS

F. A. van Goor: "Generation of Ultra-Short CO$_2$ Lasers Pulses by Mode-locking Techniques," 1984, V. A. van Goor (Enschede, NL), pp. 5, 6, 106–111.
Patent Abstracts of Japan, vol. 7, No. 32, (P-174) (1177) Feb. 8, 1983 and Japanese Patent No. 57-186158 (Suntory K. K.) Nov. 16, 1982.
Applied Optics, vol. 20, No. 18, Sep. 1981 (New York, US), A. Nicia: "Lens Coupling in Fiber-optic Devices: Efficiency Limits," pp. 3136–3145.
Patent Abstracts of Japan, vol. 3, No. 64, (E-114) May 31, 1979 and Japanese Patent No. 54-42161 (Fujitsu K. K.) Mar. 4, 1979.
Patent Abstracts of Japan, vol. 8, No. 129, (P-280) (1566) Jun. 15, 1984 and Japanese Patent No. 59-31904 (Sumitomo) Feb. 21, 1984.
Electro-Optical Systems Design, vol. 13, No. 2, Feb. 1981 (Chicago, US), R. A. Munsinger: "Fiber-optic Colorimetry," pp. 43–47.
Electronic Design, vol. 30, No. 25, Dec. 1982 (Denville, US), V. Biancomano: "Connector Workshop Addresses EMI, Shielding Standards," p. 38.

Primary Examiner—David C. Nelms
Assistant Examiner—Khaled Shami
Attorney, Agent, or Firm—Leonard A. Alkov; A. W. Karambelas

[57] ABSTRACT

The system for sensing ions in aqueous solution such as an electroplating bath includes a light source (18) which delivers light including a selected wavelength through a series of optical fibers (20, 24, 26, 32) to probe (14). The probe is partially immersed in the solution (12) and the light is delivered through the solution in the space (94) between prisms (82, 92). The return light is conducted by optical fibers (32,38) to detector or opto-electronic transducer (44). A portion of the original light is diverted by splitter (22) through fiber (42) to opto-electronic transducer (46) so that a comparison of the signals determines the amount of light in selected wavelength which is absorbed in the solution due to ions thereon. The signal processing unit (40) is preferably enclosed in an electromagnetic protected area (16) to avoid the adverse EMI and corrosive atmosphere effects near the electroplating tank (10).

12 Claims, 2 Drawing Sheets

SYSTEM FOR SENSING IONS IN AQUEOUS SOLUTION

CROSS REFERENCE

This application is a continuation of my earlier application Ser. No. 907,269, filed Sept. 15, 1986 for "System for Sensing Ions in Aqueous Solution", now abandoned.

FIELD OF THE INVENTION

This invention is directed to a system for sensing specific ions in aqueous solution, including a corrosion resistant sensor for submersion in the aqueous solution, a fiber optic system to transmit illumination of a specific wavelength to the sensor, and a fiber optic system to transmit the absorption signal back to a detector which is located in a secure environment.

BACKGROUND OF THE INVENTION

One particular environment in which the system is particularly useful is the determination of copper ion concentration in copper plating tanks. This determination has previously been accomplished by manually taking a sample of the plating solution and testing the solution in equipment simulating the electroplating environment, plating out the copper from the thereby sample solution onto an electrode. The electrode was weighed before and after the plating operation to determine the amount of copper plated out to thus derive the concentration of copper in the original plating solution. This analysis process of plating out the copper takes several hours, and the results are usually not known to the plating line operators in the plating shop for about six hours after the sample was taken. If the copper ion concentration in the plating solution falls outside the range for good copper deposition, the plating will not meet the requisite quality standards. Printed circuit boards require copper plating to build up the circuit traces after the board has been etched. If the deposited copper does not meet the requisite quality standards, the printed circuit boards must be scrapped. Thus, there is need to have current knowledge of the concentration of ions of interest in plating solution so that ion concentration can be continuously corrected to maintain a solution from which top quality electroplating can be accomplished.

SUMMARY OF THE INVENTION

In order to aid in the understanding of this invention, it can be stated in essentially summary form that it is directed to a system for sensing chemical constituents such as ions in fluid such as aqueous solution. The system comprises a light source for emitting light of a selected wavelength, an optical probe for insertion into the fluid or aqueous solution for passing light through a portion of the fluid or aqueous solution, and a light detector for sensing the amount of light that is passed through the fluid or aqueous solution, together with interconnecting optical waveguides or fibers so that the light source and light detector can be placed in a protected environment.

It is a purpose and advantage of this invention to sense chemical constituents such as ions in fluids such as aqueous solution, particularly electroplating baths, in real time so that the plating solution can be continuously monitored and corrected to provide best quality plating.

It is another purpose and advantage of this invention to provide a system which is connected together by means of fiber optics so that the optical probe may be inserted into the plating tank but the light source and light detector can be placed in an environment which is protected both from the chemical environment of the plating tank and the electrical noise of the plating tank so that the system has a long life and accurate readout in a difficult environment.

Other purposes and advantages of this invention will become apprent from a study of the following portion of this specification, the claims and the attached drawings.

DESCRIPTION OF THE PREFERRED EMBODIMENT

Electroplating tank 10 has an electroplating aqueous solution or bath 12 therein. In the preferred example, copper is the metal being plated out of the bath 12. Therefore, the bath 12 includes copper sulfate which is ionized into $Cu^{++}$ and $SO_4^{--}$. The hydrated copper complex gives the solution its characteristic blue color. The blue color is caused by light absorption in the red or near infrared portion of the spectrum. The absorption peak is at 820 nanometers wavelength in the near infrared. With other things substantially equal, the amount of light at that wavelength absorbed over a fixed path length is proportional to the concentration of the copper ions in the bath 12.

The copper plating solution bath is a difficult environment in which to perform accurate measurements. The bath is highly acidic with a pH of less than 1. The typical composition of a copper plating both is 80 grams/liter of $CuSO_4.5H_2O$ (copper sulfate pentahydrate), 10% by volume of $H_2SO_4$ sulfuric acid), 70 parts per million HCl (hydrochloric acid), 0.5% by weight of Gleam PCM (an organic wetting and brightening agent) in water as a solvent. The electroplating current is full-wave rectified alternating current, without smoothing or filtering, which produces a great deal of electrical and magnetic noise in the ambient environment around the bath. Probe 14 must be configured to withstand the chemical corrosion of the bath and must employ measurement and signal techniques which are not adversely influenced by the electrical and magnetic interference in the environment. While electronic processing is an optimum way to analyze the signals, the fact that the hydrated copper complex has an absorption peak at 820 nanometers wavelength and this peak is proportional to the copper complex in the copper plating solution 12, optical sensing is an optimum sensing method. Furthermore, optical signal transmission is a desirable way to avoid the interference from the adverse electromagnetic environment. Therefore, probe 14 is an optical probe connected to the electronic sensing equipment by means of fiber optic cables.

Figure 1:
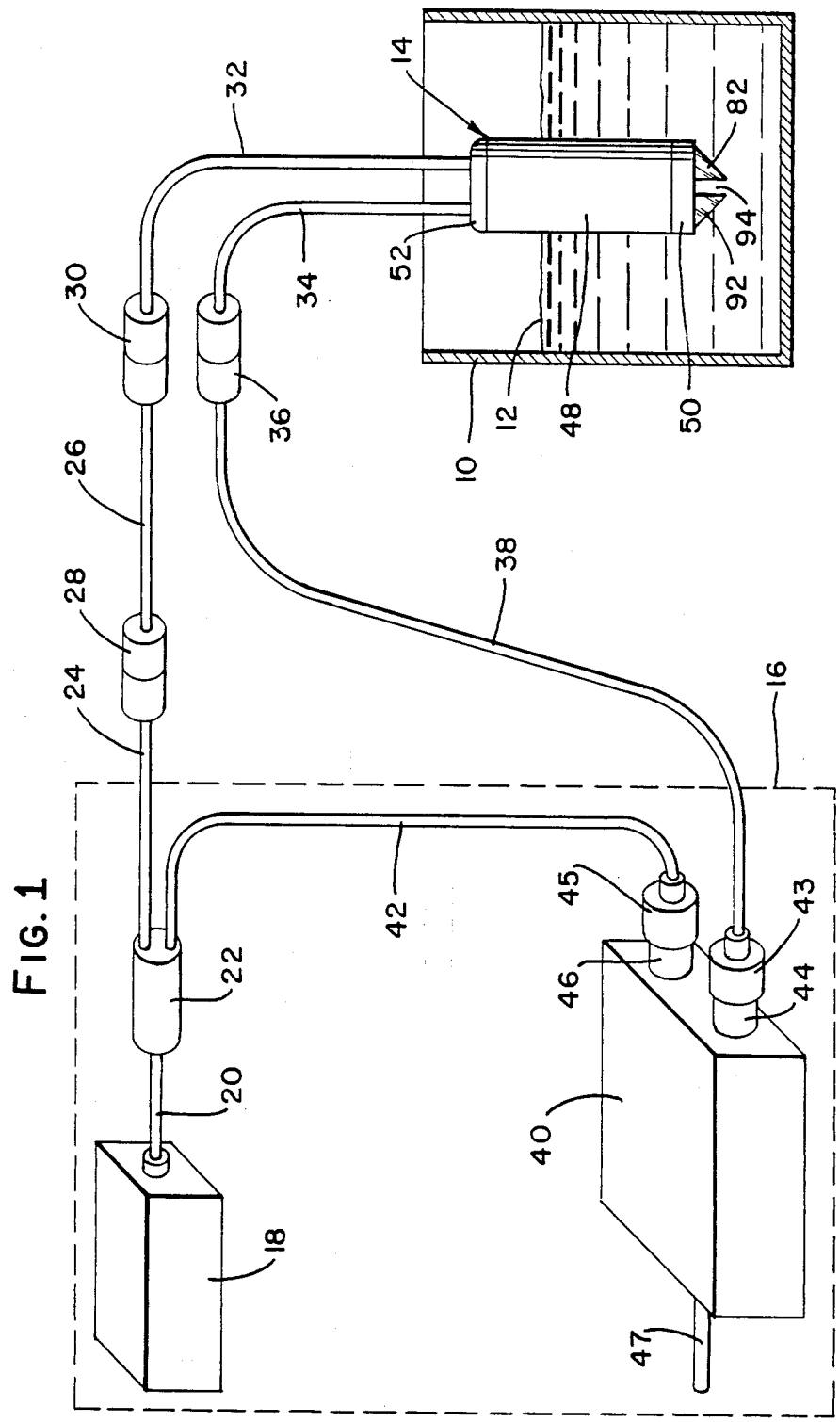
FIG. 1 is a perspective view of the system of this invention, with parts broken away.
Figure 2:
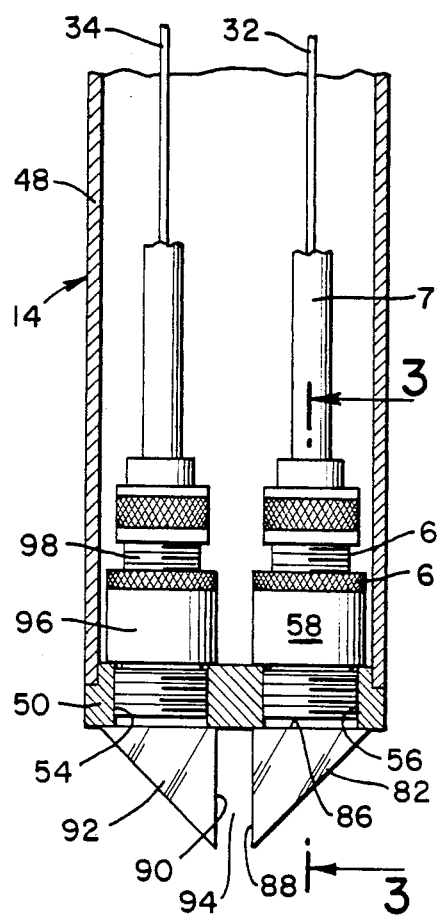
FIG. 2 is an enlarged side-elevational view of the optical probe, with parts broken away and parts taken in section.

Referring to FIG. 1, an electromagnetically protected area 16 such as a screen room contains light source housing 18 which, in turn, has a light source therein which has a sufficient output at the 820 nanometers wavelength. The area 16 protects against electromagnetic interference (EMI) as well as against corrosive atmosphere. If distances are reasonable and losses minimal, a low power light source can be employed. In the present case, the distances and losses are designed so that a light-emitting diode having an output at 820 nanometer wavelength is employed. The optical output appears in optical fiber 20 which delivers the light to optical splitter 22. A principal part of the optical output from splitter 22 is delivered to optical fiber 24 which serves as the input signal to probe 14. In the preferred example, 90% of the optical power in fiber 20 is delivered to fiber 24. Fiber 26 is a continuation thereof coupled by coupling 28. Fiber 26 is coupled through coupling 30 to the input fiber 32 to probe 14. The signal fiber 34 contains the output signal from probe 14. The signal fiber 34 is connected through coupling 36 to signal fiber 38 which is connected into the electromagnetic interference protected area 16 and is connected to the processing unit 40. The feedback fiber 42 carries the balance of the source light in fiber 20 and is also connected to processing unit 14. All fibers are single fibers and are operated as multimode optical fibers. Optical splitter 22 is conveniently formed with the fiber 20 passing straight through to come out as fiber 24 and with the fiber 42 lying thereagainst and partially fused thereto so that the feedback fiber 42 receives 10% of the original light.

Processing unit 40 has optical detectors 44 and 46 respectively connected to receive the light from fibers 38 and 42. These detectors convert the optical signals to respective electrical signals. The 10% signal feedback in feedback fiber 42 is provided so that changes in light source can be incorporated into the evaluation of the signal in fiber 38. The electronic output line 48 delivers a signal which is related only to the absorption found by probe 14.

When the light source is monochromatic, such as from a laser or a light-emitting diode, filters are not needed for achieving a narrow bandwidth source at 820 nanometers wavelength. For white light sources, including arc lamps and incandescent lamps, a narrow bandwidth filter will be needed. It is preferable that the filters 43 and 45 be placed between the fibers 38 and 42 and detectors 44 and 46 respectively so that the filters operate at a lower energy with multimode transmission.

Photodetectors which can be utilized at 820 nanometers wavelength include solid state detectors and vacuum photomultiplier devices. These devices convert the optical input signal to an electrical output signal. Solid state detectors can be used for short and medium distances where the distance between probe 14 and processing unit 40 is in the range of 10 to 100 meters. Over very long distances, such as 100 meters to 10 kilometers, photomultiplier tubes would be preferred because of their greater sensitivity. The greater sensitivity of photomultiplier tubes can be used to advantage with fibers of short to medium length, where very low concentrations of hydrated copper sulphate are to be detected. Light source fluctuations due to power line transients and temperature drift cause light source fluctuations, and these fluctuations will affect the chemical analysis unless light source feedback is employed. Splitting the beam through fiber 42 and utilizing a sample of the light source fed directly to the detector 46 eliminates that problem.

Figure 3:
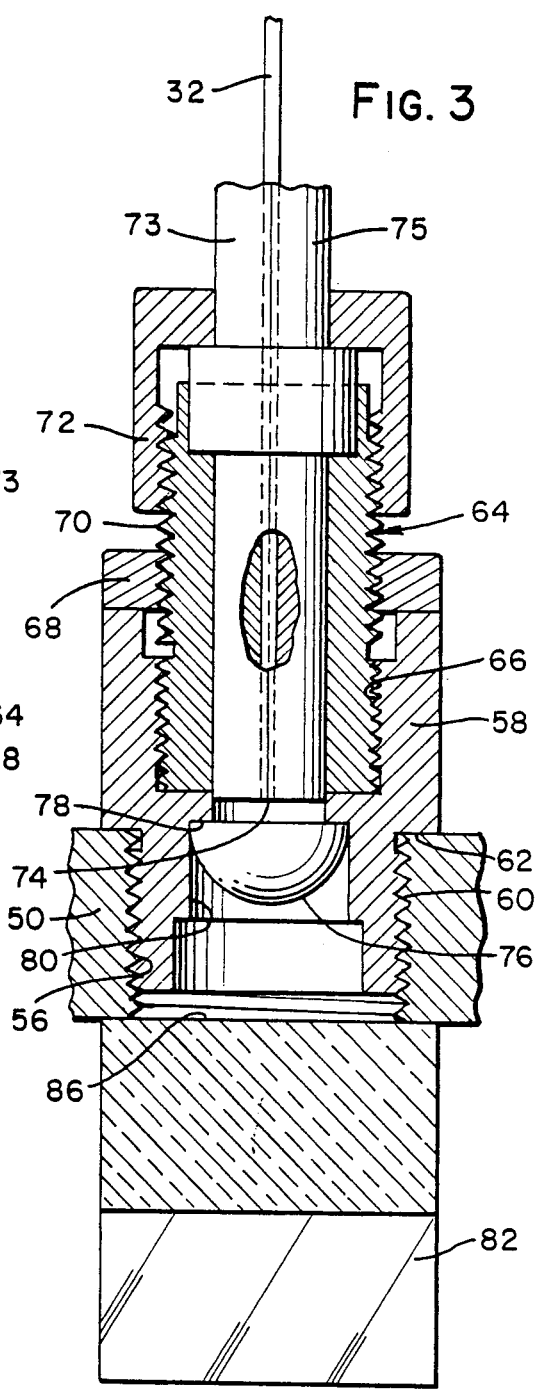
FIG. 3 is a further enlarged section taken generally along line 3—3 of FIG. 2.

The probe 14 serves as an interface between the plating solution 12 and the light in the optical fibers 32 and 34. Since the plating solution 12 is an adverse environment for structures, in view of its acidity, the structure of the probe is carefully configured to provide a reasonable life for the probe. Casing 48 is closed on its front end by front plate 50 and its upper end by cap 52. As is seen in FIG. 1, the cap has openings therein for passage therethrough of the fibers 32 and 34. The cap is sealed around the fibers. Front plate 50 has threaded openings 54 and 56 therein. As seen in FIG. 3, lens carrier 58 is screwed into the opening 56. Lens carrier 58 has screw threads 60 which engage in threaded opening 56 and has a shoulder 62 which engages against the top surface of front plate 50 so that the lens carrier 58 can be firmly screwed into place and sealed to prevent leakage through the opening 56. Connection adaptor 64 carries fine threads on its lower end which engage in the threaded recess 66 in the top of lens carrier 58. Lock nut 68 engages on more coarse threads 70 on the upper end of the adaptor 64. The threads 70 are configured to receive connector nut 72. Connector nut 72 engages on the halves 73 and 75 of the clamp sleeve which clamp to the outer end of input fiber 32. Fine threads 66 are provided so that up and down adjustment can be made of the connector adaptor 64 to control the position of the end 74 of input fiber 32.

In the present case, the end is shown with a small gap between the fiber and the flat side of hemispherical lens 76. The lens is secured against shoulder 78 in the bottom of lens recess 80. Prism 82 is mounted on and sealed against the front of front plate 50. Prism 82 is a conventional 5-sided orthogonal prism with two sides at right angles and with the angular face preferably at a 45° angle with respect to both orthogonal faces. Input face 86 is at right angles to output face 88. The output face 88 is spaced from and parallel to the input face 90 of prism 92. The input and output faces define space 94 therebetween. Behind lens 92 is a lens carrier 96 which is identical to lens carrier 58 and a connection adaptor 98 identical to connection adaptor 64 to thus connect the prism 92 to signal fiber 34.

When the probe 14 is placed in a plating bath solution 12, as seen in FIG. 1, and the system is energized, light at 820 nanometers is delivered to fiber 32 and the fiber 32 delivers it through prism 82 and across gap 94. The plating bath solution 12 occupies the gap 94 and the amount of light transmitted across the space 94 is a function of the absorption of the bath materials in that part of the spectrum. The 820 nanometer wavelength is chosen because it is the peak absorption of the hydrated copper complex in the bath. Therefore, the amount of light absorbed and, consequently, the amount of light transmitted into prism 92 is a function of the concentration of the hydrated copper complex. The signal in signal fiber 34 and the signal in signal fiber 38 to the optical detector 44 is thus related to the amount of hydrated copper complex in the bath. As previously described, changes in the light source are compensated by the light in the feedback fiber 42. The optical information is converted to electronic signals in detectors 44 and 46, and the electronic signals are processed in unit 40 to provide a signal in output line 47 which is a signal to the operator giving him the state of concentration of the hydrated copper complex in the bath.

The preferred structural embodiment of this invention has been described as being utilized for the sensing of copper ion concentration in a copper plating bath. By choice of a particular wavelength to be transmitted across the gap 94, and related light source, filter and detector characteristics, the system can be used in other baths to detect other materials. Tin-lead electroplating baths employ Peptone to improve the plating quality. Peptone is an animal organic material which acts as a wetting agent and as a brightener in such baths. Solder is electroplated onto solder pads on which electronic components will be surface-mounted. Solder plating baths contain several hazardous materials so that taking samples requires extreme caution. Fluboric acid ($HBF_4$) is one of the few materials in which eutectic tin-lead solder will dissolve. Without the addition of Peptone, the tin-lead plates out with a grey surface appearance and is brittle in bend testing. The addition of Peptone eliminates the brittleness and causes the tin-lead solder to plate out with a bright surface.

Peptone is a complex organic, and it is not known which component or components thereof cause the improvement in plating characteristics. However, it has been determined that the organic constituents in the Peptone which are favorable to plating absorb ultraviolet light in the range of 200 to 360 nanometers. Thus, by employing the probe 14 and the system, the effective Peptone concentration can be measured. When the probe 14 is used in this range, the light source in housing 18 is preferably a deuterium arc lamp, which has a significant ultraviolet output. The optical splitter, fibers and probe are the same as previously described. Filters 43 and 45 pass ultraviolet in the range of 200 to 360 nanometers, and preferably in the more narrow range of 300 to 340 nanometers. In this narrower range, it has been determined that there was a larger change in detected light absorption with changes in Peptone concentration. In this way, real time analysis of Peptone in lead-tin solder plating solutions is achieved, to maintain solder plating solution balance, increase production efficiency, and decrease danger to personnel by eliminating sampling. This advantage of successful sampling is achieved by employment of the clad single fibers so that an adequate distance between the probe and the electromagnetic interference protected instrumentation can be achieved.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A system for sensing a chemical constituent which has a predetermined optical absorption peak in a fluid comprising:
   light source means for producing light including a wavelength substantially at the absorption peak of the constituent to be sensed;
   a probe for insertion into the fluid to be tested for the constituent;
   a first flexible optical waveguide connecting said light source with said probe so that said light source is away from said probe and the fluid;
   a first optical detector sensitive to the wavelength of the absorption peak;
   a second flexible optical waveguide connecting said probe with said first optical detector;
   signal processing means connected to said optical detector for processing an electrical analog of the optical signal received by said first detector;
   said probe comprising:
   a hollow casing having a front end and a cap end;
   a front plate enclosing said front end of said casing, said front plate having an outside and an inside, said front plate having first and second openings therethrough from said outside to said inside;
   first and second prisms mounted on the outside of said front plate to respectively cover said first and second openings therein, said prisms having faces facing each other and spaced from each other to define a space therebetween;
   first and second couplings mechanically and optically connecting said first and second optical waveguides with respect to said first and second openings in said front plate, first and second lens carriers respectively secured over said first and second openings in said front plate on the interior side of said front plate, first and second lenses, said first and second lenses being respectively mounted on said first and second lens carriers and positioned respectively between said first and second waveguides and said first and second prisms, said first and second optical waveguides being mounted with respect to said first and second lens carrier, said first and second couplings being adjustable so that light in said first waveguide can illuminate said first prism and direct light across said space between said first and second prisms and light received by said second prism is directed into said waveguide as modified by the optical absorption of the fluid within said space.

2. The system of claim 1 wherein there is a second optical detector connected to said processing unit and there is a third optical waveguide connected between said light source and said second optical detector to feed to said processing unit a signal corresponding to said light source.

3. The system of claim 2 wherein a first lens is positioned between said first optical waveguide and said first prism and a second lens is positioned between said second optical waveguide and said second prism.

4. A system for sensing a chemical constituent which has a predetermined optical absorption peak in a fluid comprising:
   light source means for producing light including light at a wavelength at the absorption peak of the constituent to be sensed;
   a probe for insertion into the fluid to be tested for the constituent, said probe comprising a hollow casing with a front plate secured to the front end of said casing to enclose the front end of said probe, said front plate having first and second openings therein;
   a first flexible optical waveguide connecting said light source with said probe so that said light source is away from said probe and the fluid;
   a first optical detector sensitive to the wavelength of the absorption peak;
   a second flexible optical waveguide connecting said probe with said first optical detector;
   signal processing means connected to said optical detector for processing an electrical analog of the optical signal received by said first detector;
   said probe comprising:
   a hollow casing having a front end and a cap end;

a front plate enclosing said front end of said casing, said front plate having an outside and an inside, said front plate having first and second openings therethrough from said outside to said inside;

first and second prisms mounted on the outside of said front plate to respectively cover said first and second openings therein, said prisms having faces facing each other and spaced from each other to define a space therebetween;

first and second couplings mechanically and optically connecting said first and second optical waveguides with respect to said first and second openings in said front plate, first and second lens carriers respectively secured over said first and second openings in said front plate on the interior side of said front plate, first and second lenses, said first and second lenses being respectively mounted on said first and second lens carriers and positioned respectively between said first and second waveguides and said first and second prisms, said first and second optical waveguides being mounted with respect to said first and second lens carrier, said first and second couplings being adjustable so that light in said first waveguide can illuminate said first prism and direct light across said space between said first and second prisms and light received by said second prism is directed into said waveguide as modified by the optical absorption of the fluid within said space.

5. The system of claim 4 wherein first and second connection adaptors are respectively attached to said front plate interiorly of said casing and in respectively alignment with said first and second openings in said front plate, said first and second optical waveguides being disconnectably attached to said first and second connection adaptors.

6. The system of claim 5 wherein said first and second lenses respectively are positioned with respect to said first and second prisms and said connection adaptors are respectively threaded to permit focus adjustment of said respective first and second fibers with respect to said first and second lenses to optimize optical coupling between said fibers and said prisms.

7. The system of claim 6 wherein there is a second optical detector connected to said processing unit and there is an optical waveguide connected between said light source and said second optical detector to feed to said processing unit a signal corresponding to said light source.

8. The system of claim 7 wherein said probe carries first and second prisms and said first and second optical waveguides are respectively connected to said first and second prisms, said space being positioned between prism faces.

9. A probe for insertion into a fluid having a constituent with a predetermined optical absorption peak comprising:

a hollow casing having a front end and a cap end;

a front plate enclosing said front end of said casing, said front plate having an outside and an inside, said front plate having first and second openings therethrough from said outside to said inside;

first and second prisms mounted on the outside of said front plate to respectively cover said first and second openings therein, said prisms having faces facing each other and spaced from each other to define a space therebetween;

first and second flexible optical waveguides;

first and second couplings mechanically and optically connecting said first and second optical waveguides with respect to said first and second openings in said front plate, first and second lens carriers respectively secured over said first and second openings in said front plate on the interior side of said front plate, first and second lenses, said first and second lenses being respectively mounted on said first and second lens carriers and positioned respectively between said first and second waveguides and said first and second prisms, said first and second optical waveguides being mounted with respect to said first and second lens carrier, said first and second couplings being adjustable so that light in said first waveguide can illuminate said first prism and direct light across said space between said first and second prisms and light received by said second prism is directed into said waveguide as modified by the optical absorption of the fluid within said space.

10. The system of claim 9 wherein first and second connection adaptors are respectively threadedly engaged in said first and second lens carriers, said first and second optical waveguides being respectively attached to said first and second connection adaptors.

11. The system of claim 9 wherein there are first and second connection adaptors respectively threaded with respect to said first and second lens carriers, said first and second waveguides being respectively attached to said first and second connection adaptors so that the position of said first waveguide can be adjusted with respect to said first lens by threaded engagement of said first connection adaptor within said first lens carrier and said second waveguide can be adjusted with respect to said second lens by threaded engagement of said second connection adaptor within said second lens carrier.

12. The system of claim 11 wherein first and second lock nuts respectively interengage between said first and second connection adaptors and said first and second lens carriers.

* * * * *